United States Patent
Ostiguy et al.

[11] Patent Number: 5,879,403
[45] Date of Patent: Mar. 9, 1999

[54] BISTABLE CEMENT RESTRICTOR

[75] Inventors: Pierre S. Ostiguy, Rochester; Brooke W. Mastrorio, Lakeville, both of Mass.

[73] Assignee: Johnson & Johnson Professional, Inc., Raynham, Mass.

[21] Appl. No.: 828,035

[22] Filed: Mar. 27, 1997

[51] Int. Cl.[6] ............................................. A61F 2/32
[52] U.S. Cl. .................................... 623/22; 623/16
[58] Field of Search ............................. 623/22, 23, 16; 606/60–62, 92–95

[56] References Cited

U.S. PATENT DOCUMENTS

| | | | |
|---|---|---|---|
| 4,245,359 | 1/1981 | Stuhmer | 3/1.9 |
| 4,276,659 | 7/1981 | Hardinge | 3/1.9 |
| 4,302,855 | 12/1981 | Swanson | 3/1.9 |
| 4,344,190 | 8/1982 | Lee et al. | 3/1.9 |
| 4,447,915 | 5/1984 | Weber | 3/1.9 |
| 4,462,394 | 7/1984 | Jacobs | 128/92 C |
| 4,559,936 | 12/1985 | Hill | 128/92 R |
| 4,686,973 | 8/1987 | Frisch | 128/92 YZ |
| 4,697,584 | 10/1987 | Haynes | 128/92 VQ |
| 4,745,914 | 5/1988 | Frey et al. | 128/92 VP |
| 4,904,267 | 2/1990 | Bruce | 623/23 |
| 5,061,288 | 10/1991 | Berggren | 623/23 |
| 5,092,891 | 3/1992 | Kummer et al. | 623/16 |
| 5,326,376 | 7/1994 | Warner | 623/23 |
| 5,340,362 | 8/1994 | Carbone | 623/23 |
| 5,376,120 | 12/1994 | Sarver | 623/16 |
| 5,383,932 | 1/1995 | Wilson | 623/16 |
| 5,531,792 | 7/1996 | Huene | 606/95 |
| 5,549,694 | 8/1996 | Noiles et al. | 623/22 |
| 5,645,589 | 7/1997 | Li | 606/95 |
| 5,662,657 | 9/1997 | Carn | 606/95 |

OTHER PUBLICATIONS

Brochure entitled *Cemented Hip Systems Surgical Technique*, Johnson & Johnson Orthopaedics, pp. 1–9, dated May 1996.

*Primary Examiner*—Michael J. Milano
*Attorney, Agent, or Firm*—Nutter, McClennen & Fish, LLP

[57] ABSTRACT

A bistable cement restrictor is provided for creating a fixed obstruction at any selected point within a long bone, particularly at points beyond the isthmus of the bone. An exemplary cement restrictor includes a body having a first end and a second end. One or more bistable fins extend radially from the body and are movable from a first stable state to a stable state either mechanically or thermally. In the first stable state, the cement restrictor is narrower than in the second stable state. While the cement restrictor is readily transitionable from the first stable state to the second stable state, the transition can be irreversible.

20 Claims, 3 Drawing Sheets

BISTABLE CEMENT RESTRICTOR

CROSS REFERENCE TO RELATED APPLICATIONS

Non applicable

STATEMENT REGARDING FEDERALLY-SPONSORED RESEARCH

Non applicable

FIELD OF THE INVENTION

The present invention relates to a device used in hip arthroplasty, and more particularly to a bistable structure for creating a cement restriction or blockage within a medullary canal of a long bone.

BACKGROUND OF THE INVENTION

Arthroplasty procedures, such as a total hip replacement, can require the removal of the femoral head and neck, followed by implantation of an artificial hip stem into a reamed portion of the femoral medullary canal. Some hip arthroplasty procedures call for the use of bone cement to secure the hip stem within the medullary canal. For procedures that call for cement, it is generally undesirable to allow the cement to infiltrate the medullary canal to an uncontrolled depth and volume. Therefore, a hip arthroplasty procedure can include the step of placing an obstruction within the medullary canal in an attempt to restrict or block the flow of cement.

Not infrequently, the obstruction is merely a partially hardened or cured ball of cement placed into the canal and held in place by friction fit with the wall of the canal. This makeshift obstruction is easily dislodged by the distal end of the hip stem if the cement ball is not inserted deep enough into the canal. Additionally, the ball of cement is readily displaced when pressurized cement is added to the medullary canal to bind the stem in place. If the cement ball is fractured and/or if it falls beyond a narrow central region of the femur known as the isthmus, the pressurized cement does not properly infiltrate the bone and air pockets or pores are created in the cement. The imperfection laden hardened cement thus provides a poor interlock with the bone and stem and it is susceptible to cracking. Poor mechanical interlock and cement failure causes the stem to loosen. This undesirable occurrence often requires that the joint be replaced in a procedure known as a revision.

Revision surgery and/or procedures requiring a "long" hip stem are especially problematic with an application that calls for pressurized cement. Specifically, the distal end of a revision stem ultimately extends further into the medullary canal than an original "normal" stem because additional bone is cut-away during removal of the original stem in preparation to prepare for implantation of the revision stem, or poor quality bone stock forces a larger stem to be used to secure the stem more distally in the canal to reach better quality bone to achieve implant stability. Whereas the distal end of the original stem may extend to a point before or above the isthmus, and thus above the ball of cement, the distal end of the revision stem may extend beyond the isthmus.

Structures other than cement balls are also known for creating a blockage within a medullary canal. For example, FIG. 1 illustrates a known device 10 including a tapered body 12 having a first end 14, a second end 16, and fins 18 that extend radially from the body. Each fin 18 is resilient and can be flexed toward the first end 14 or the second end 16 of the body 12 as shown in the illustration by dashed lines. Although it is possible to maintain one or more fins 18 in a flexed condition by applying pressure to the fin(s) or placing them in a confined space to elastically deform them, once the pressure is relieved or the device is removed from confinement, the fin(s) will always return to their original position unless they have been plasticlly deformed. Thus, the fins 18 and the device 10 can be described as only having a single stable state.

In use, a single stable state device 10 can be well suited to the tasks of creating a blockage within a reamed medullary canal 20 above an isthmus region 22 as shown in FIG. 2. It will be noted that the fins 18 are deformed different amounts depending on where they are within the tapered medullary canal 20. The body 12 and the fins 18 can have a thickness such that even when the fins are fully compressed against the body, the device 10 is broader than the isthmus 22 to prevent the device from being readily pushed beyond the isthmus. Thus, in a typical pressurized cement application, the pressurization of the cement does not dislodge the device.

By contrast with an above-the-isthmus application, the device 10 is totally unsuited for beyond-the-isthmus applications as shown in FIG. 3. Specifically, once some of the fins 18 of the device 10 move beyond the isthmus, there is less and less mechanical interlock with the bone and even the application of low pressure causes the plug to be dislodged. Were the device 10 to be deliberately passed beyond the isthmus and then pulled back up into the narrow passage as shown in FIG. 4, the flexed fins 18 would urge the device down and away from the isthmus.

SUMMARY OF THE INVENTION

The present invention overcomes the disadvantages of known techniques and devices by providing a cement restrictor that is particularly well suited for revision arthroplasty. An appropriately dimensioned cement restrictor can create a fixed obstruction at any selected point within a long bone, particularly at points beyond the isthmus.

The cement restrictor includes a single or multiple finned body having a first stable state and a second stable state. In the first stable state, the cement restrictor is narrower than in the second stable state. While the cement restrictor is readily transitionable from the first stable state to the second stable state, the transition can be irreversible.

An illustrative embodiment of the cement restrictor includes a body having a first end and a second end. Bistable fins extend radially from the body and are irreversibly movable from a first stable state to a second stable state. The fins are concave with respect to the first end of the body in the first stable state and convex with respect to the first end of the body in the second stable state. The diameter of each fin is larger in the second stable state than in the first stable state.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein.

DETAILED DESCRIPTION OF THE INVENTION

Figure 1:
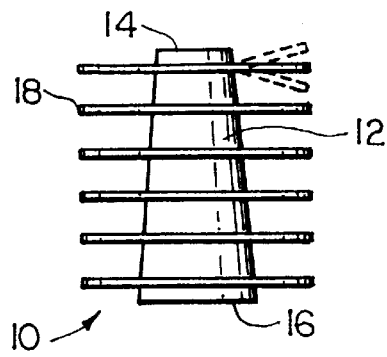
FIG. 1 is an elevational view of a prior art cement restrictor.
Figure 3:
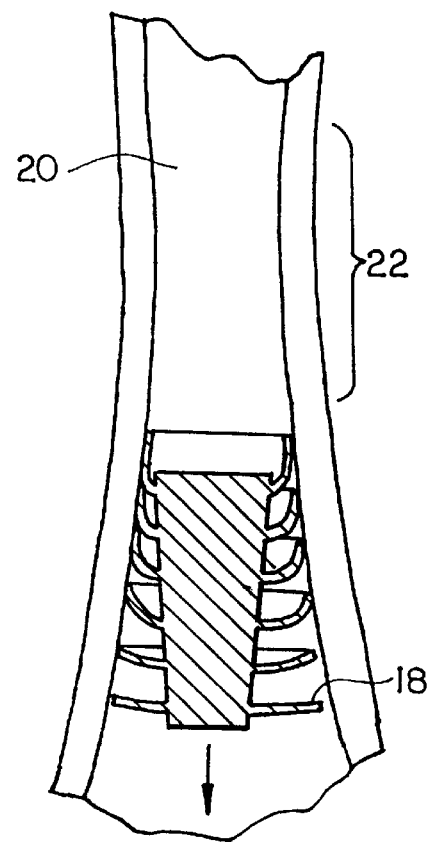
FIG. 3 is a sectional view of a reamed bone, wherein the prior art cement restrictor of FIG. 1 has been pushed beyond the isthmus of the bone.
Figure 2:
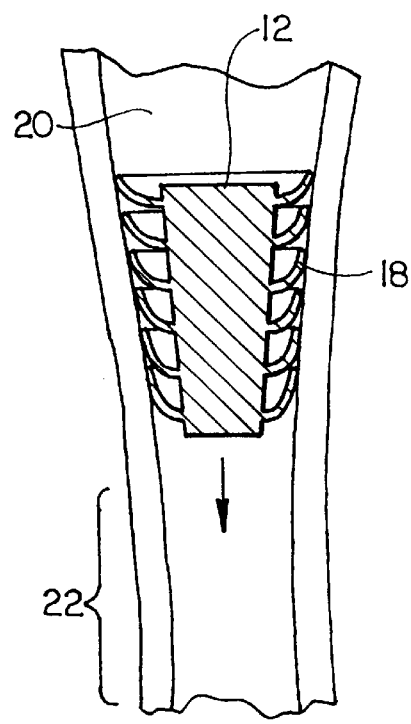
FIG. 2 is a sectional view of a reamed bone, wherein insertion of the prior art cement restrictor of FIG. 1 is depicted.
Figure 4:
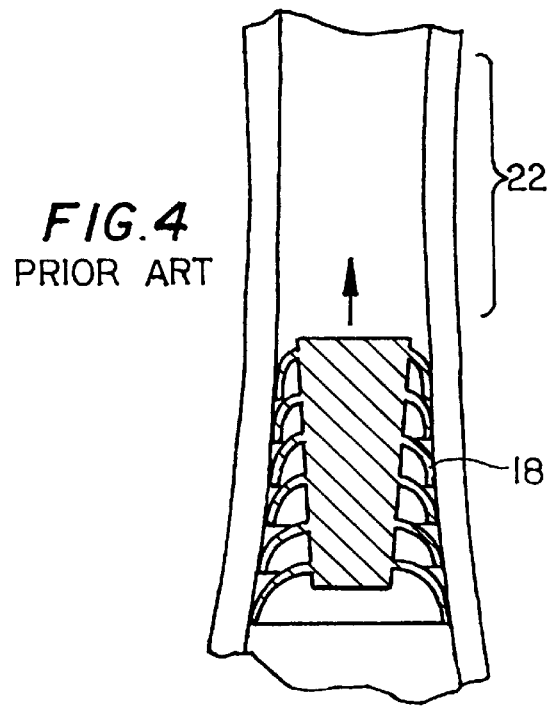
FIG. 4 is a sectional view of a reamed bone, wherein the prior art cement restrictor of FIG. 1 has been pushed completely beyond the isthmus and is being pulled back toward the isthmus.
Figure 5:
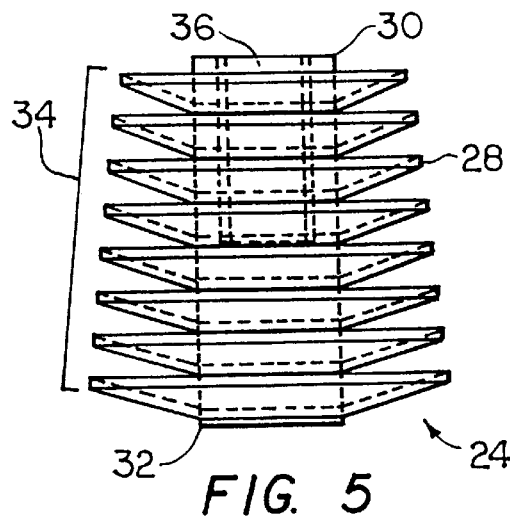
FIG. 5 is an elevational view of a cement restrictor in accordance with the present invention in a first stable state.
Figure 6:
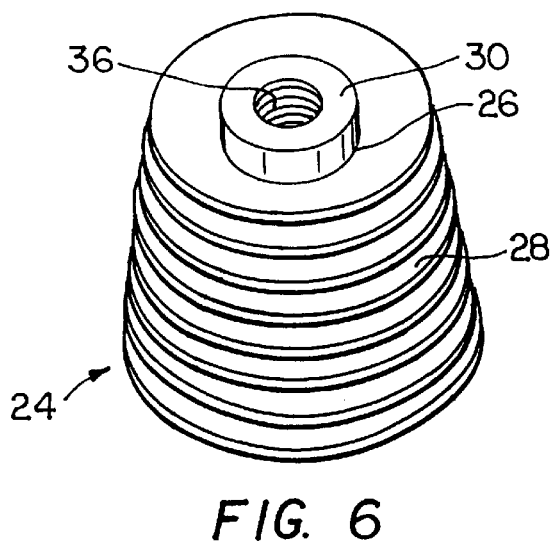
FIG. 6 is a perspective view of the cement restrictor of FIG. 5.

FIGS. 5 and 6 are side and perspective views, respectively, of a cement restrictor 24 in accordance with the invention that includes a body 26 from which one or more fins 28 extend radially in a first stable state. As used herein, "stable state" means a condition in which a structure(s) (e.g., the fins) retains a predetermined shape, configuration, or orientation with respect to another element(s) (e.g., the body); and even if the structure(s) is deformed within a selected range of deformation, the structure(s) will rebound or return to the predetermined shape or configuration in the absence of additional or externally applied energy or forces. For example, as described in greater detail below, it can be possible to deform the fins 28 by applying pressure to them in a first direction, and upon discontinuance of the pressure, the fins return to their pre-deformation orientation; whereas applying pressure to the fins in a second direction causes the fins to be deformed such that after the pressure has been discontinued, the fins do not return to their pre-deformation orientation.

Continuing to refer to FIGS. 5 and 6, an elongate body 26 has a first end 30, a second end 32, and an intermediate portion 34 between the first and second ends. Although each fin 28 can be identically dimensioned, the exemplary fins 28 are of different diameters. For example, the fin 28 near the first end of the body has the smallest diameter and the fin nearest the second end has the greatest diameter. Each successive fin 28 from the first end of the body to the second end thereof is broader than the preceding fin. Thus, because the body 26 has a uniform diameter, the cement restrictor 24 has a tapered profile. The specific fin dimensions and the overall profile of the cement restrictor 24 are determined by the anticipated medullary wall contours at an intended site of obstruction. For an embodiment of the cement restrictor having fins 28 of different diameters, but having substantially uniform thickness, the broader fins are more flexible than the less broad fins to allow the fins to be deformed enough to fit through an opening of a selected size, such a reamed isthmus. However, the spacing of the fins 28 from each other inhibits the fins from being excessively deformed.

Figure 7:
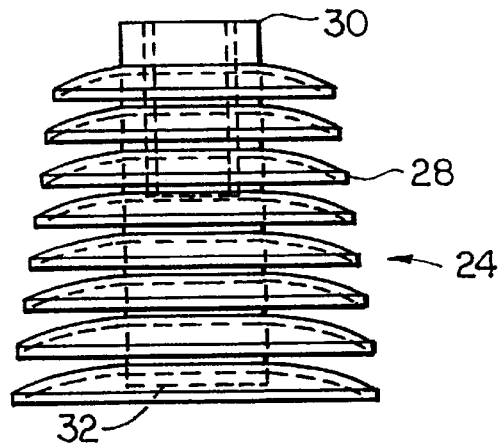
FIG. 7 is an elevational view of the cement restrictor of FIGS. 5 and 6, showing the cement restrictor in a second stable state.
Figure 10:
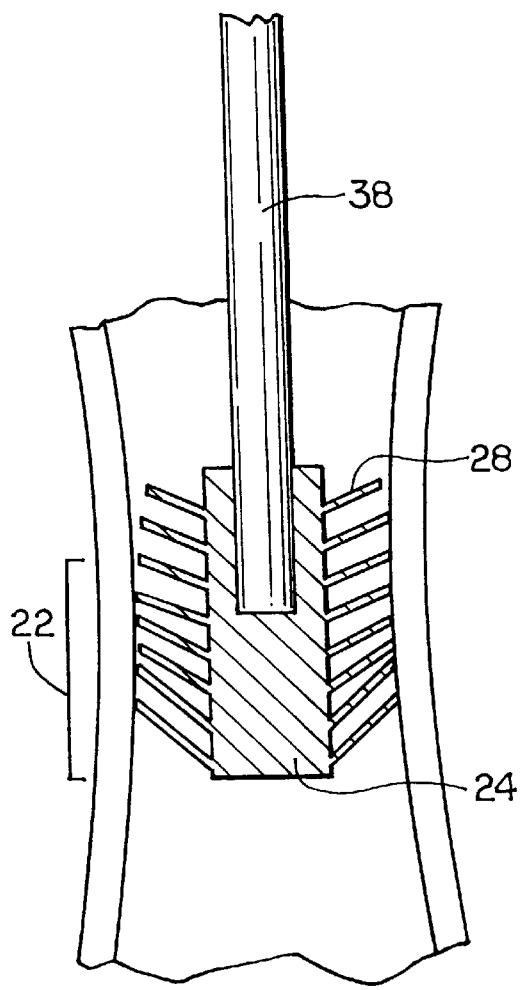
FIG. 10 shows an exemplary cement restrictor in accordance with the invention being inserted into a reamed bone portion, wherein the cement restrictor is in a first stable state.
Figure 11:
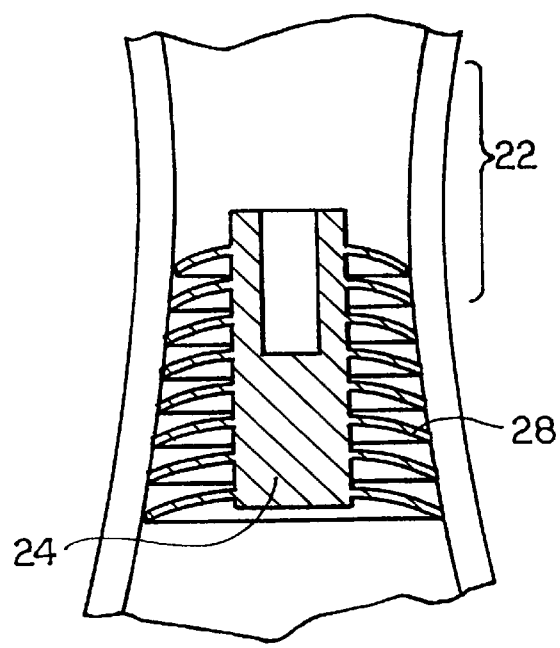
FIG. 11 depicts the cement restrictor of FIG. 10 in an installed configuration beyond the isthmus, wherein the cement restrictor is in a second stable state.

It should be noted that while axial pressure applied to the body 26 in the direction of the second end of the body, or axial pressure applied to the fins in the direction of the first end of the body, or a combination thereof, can cause the fins 28 to be deformed, as shown in FIG. 10, the cement restrictor 24 remains in the first stable state. By contrast, axial pressure applied to the body in the direction of the first end of the body, or axial pressure applied to the fins in the direction of the second end of the body, or a combination thereof, can cause the fins to be deformed, as shown in FIG. 7, to transition the cement restrictor from the first stable state to the second stable state. The first stable state of the cement restrictor is notable for the fins 28 being angled toward the first end of the body or fins which are convex with respect to the second end of the body to facilitate insertion of the cement restrictor into a medullary canal. In its second stable state, shown in FIG. 7, the cement restrictor 24 is notable for the angulation of the fins toward the second end of the body or fins which are concave with respect to the second end of the body to inhibit movement of the cement restrictor with respect to the bone as shown in FIG. 11. The cement restrictor can be configured so as to be irreversible. In other words, it cannot be transitioned from the second stable state to the first stable state. However, even in the second stable state the fins can flex, yet return or urge to return to the predetermined configuration or shape that defines the second stable state.

The embodiment of the cement restrictor shown in FIGS. 5–7 includes eight fins 28. Although the number of fins many be different for other embodiments, and can be as few as a single fin, it is desirable to have a large number of fins to maximize the surface for mechanical interlock between the fins and the bone, to ensure that the cement restrictor does not become displaced during subsequent cement pressurization.

In an exemplary embodiment, the fins 28 are made of a resilient material such as polyethylene and they are joined to or are integral with the body 26 so as to be bistable as described above. However, the fins 28 can also be made of a temperature responsive, stress responsive, or super elastic shape memory alloy (SMA). Thus, the fins 28 can be in the first stable state at a first temperature or stress condition and in the second stable state at a second temperature or stress condition. In an exemplary embodiment, the cement restrictor is chilled to below (or heated above) body temperature to place it in the first stable state, at which point the cement restrictor is readily insertable into a bone. As the fins warm (or cool) to a temperature in the normal range of body temperatures, the fins transition to the second stable state and engage the bone. Additionally, even though the fins are shown as discrete elements, other embodiments include a single, helical fin.

Continuing to refer to FIG. 5 and 6, the body 26 can include an engagement feature to allow it to be manipulated with surgical tools to position the cement restrictor and to transition it from the first stable state to the second stable state. As illustrated, the body 26 includes a recess or socket 36 into which a tool 38 (shown in FIG. 10) can be inserted to push the cement restrictor 24 through the medullary canal and with which axial pressure can be applied to the body. The socket 36 can include a resilient surface or sleeve to help temporarily hold the tool 38 in an engaged relationship with the cement restrictor 24. In another embodiment, the socket 36 and the tool 38 are threaded. The specific features of the tool and its engagement with the cement restrictor are not of particular importance with respect to the present invention.

Figure 8:
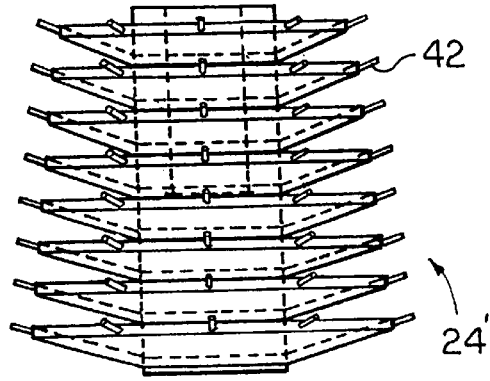
FIG. 8 is an elevational view of an alternative embodiment of a cement restrictor in accordance with the invention in a first stable state.
Figure 9:
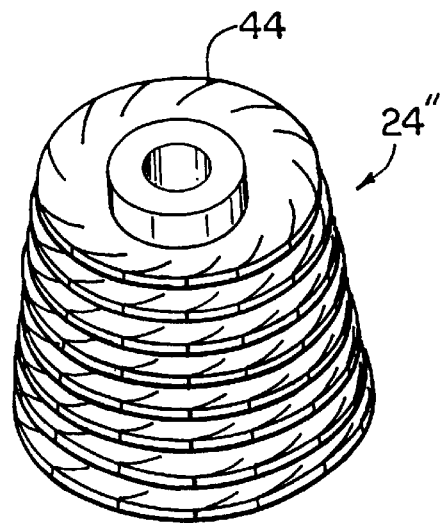
FIG. 9 is an perspective view of yet another embodiment of a cement restrictor in accordance with the invention in a first stable state.

Although fins 28 in the second stable state are capable of holding the cement restrictor 24 in place within a bone, other embodiments include fins with roughened peripheral regions, such as the edge of the fin and an adjacent surface portion. In yet other embodiments, such as shown in FIG. 8, barbs 42 can extend from the periphery of one or more fins. The cement restrictor can be twisted to cause the barbs to dig into the bone. FIG. 9 illustrates yet another embodiment of the cement restrictor adapted to enhance interlock with a bone surface, wherein cuts 44 extend radially through one or more fins. When the cement restrictor is twisted, the fins separate at the cuts and the edges of the fins dig into the bone.

FIG. 10 illustrates the an exemplary cement restrictor 24 in accordance with the invention being pushed into a medullary canal with an insertion tool 38. The cement restrictor is in a first stable state and deformation of fins 28 at the isthmus region should be noted.

FIG. 11 shows the cement restrictor of FIG. 5 in place beyond the isthmus. The insertion tool 38 (or other tool) has applied a tractive axial force to the body to cause the fins to transition to a second stable state, and the cement restrictor is shown in the second stable state with the tool(s) removed. The fins engage the bone wall with sufficient force to permit pressurized cement to be added to the medullary canal in a manner known to those skilled in the art without dislodging the cement restrictor.

Although the invention has been shown and described with respect to exemplary embodiments thereof, various other changes, omissions and additions in form and detail thereof may be made without departing from the spirit and scope of the invention.

What is claimed is:

1. A cement restrictor comprising:
a configurable structure having a first configuration that has a diameter with respect to a selected axis and a second configuration that has a second diameter with respect to the selected axis, the second diameter being greater than the first diameter,
wherein the configurable structure includes a body having a first end and a second end; and a plurality of bistable fins extending radially from the body and being movable from a first stable state to a second stable state.

2. The cement restrictor of claim 1, wherein transition of the bistable fins from the first stable state to the second stable state increases the diameter of the cement restrictor.

3. The cement restrictor of claim 1, wherein the fins are concave with respect to the first end of the body in the first stable state and wherein the fins are convex with respect to the first end of the body in the second stable state.

4. The cement restrictor of claim 1, wherein the fins define an acute angle with respect to the first end of the body in the first stable state and wherein the fins define an obtuse angle with respect to the first end of the body in the second stable state.

5. The cement restrictor of claim 1, wherein transition of the fins from the first stable state to the second stable state is irreversible.

6. The cement restrictor of claim 1, wherein the fins are transitioned from the first stable state to the second stable state by applying axial pressure to one of the body and the plurality of fins.

7. The cement restrictor of claim 1, wherein each fin has a different diameter than the other fins of the plurality of fins.

8. The cement restrictor of claim 1, wherein the fins are resilient in the first and second stable states.

9. A cement restrictor comprising:
a configurable structure having a first configuration that has a diameter with respect to a selected axis and a second configuration that has a second diameter with respect to the selected axis, the second diameter being greater than the first diameter,
wherein the configurable structure includes a body having a first end and a second end and a plurality of bistable fins extending radially from the body and being movable from a first stable state to a second stable state, and
wherein the fins include a shape memory alloy.

10. The cement restrictor of claim 9, wherein the fins are thermally transitioned from the first stable state to the second stable state.

11. The cement restrictor of claim 9, wherein a stress applied to the fins is changed from a first stress level to a second stress level to transition the fins from the first stable state to the second stable state.

12. A cement restrictor comprising:
a configurable structure having a first configuration that has a diameter with respect to a selected axis and a second configuration that has a second diameter with respect to the selected axis, the second diameter being greater than the first diameter,
wherein the configurable structure includes a body having a first end and a second end and a plurality of bistable fins extending radially from the body and being movable from a first stable state to a second stable state, and
wherein at least one of the fins includes barbs extending therefrom.

13. A cement restrictor comprising:
a configurable structure having a first configuration that has a diameter with respect to a selected axis and a second configuration that has a second diameter with respect to the selected axis, the second diameter being greater than the first diameter,
wherein the configurable structure includes a body having a first end and a second end and a plurality of bistable fins extending radially from the body and being movable from a first stable state to a second stable state, and
wherein at least one the fins includes a plurality of radial cuts through the fin.

14. A cement restrictor comprising:
a body having a first end and a second end; and
a plurality of bistable fins extending radially from the body and being irreversibly movable from a first stable state to a second stable state,
wherein the fins are concave with respect to the first end of the body in the first stable state,
wherein the fins are convex with respect to the first end of the body in the second stable state, and
wherein the diameter of each fin is larger in the second stable state than in the first stable state.

15. The cement restrictor of claim 14, wherein a portion of each fins is axially movable with respect to the body.

16. The cement restrictor of claim 14, wherein the fins are thermally transitioned from the first state to the second state.

17. The cement restrictor of claim 14, wherein a stress applied to the fins is changed from a first stress level to a second stress level to transition the fins from the first stable state to the second stable state.

18. The cement restrictor of claim 14, wherein the fins are resilient in the first and second stable states.

19. The cement restrictor of claim 14, wherein at least one of the fins includes barbs extending therefrom.

20. The cement restrictor of claim 14, wherein at least one the fins includes a plurality of radial cuts through the fin.

* * * * *